United States Patent [19]

Elam et al.

[11] Patent Number: 5,359,880
[45] Date of Patent: Nov. 1, 1994

[54] FIBER MICRONAIRE MEASURING APPARATUS AND METHOD

[75] Inventors: Francis E. Elam; Larry E. Teague, both of Dallas, Tex.

[73] Assignee: Motion Control, Inc., Dallas, Tex.

[21] Appl. No.: 121,745

[22] Filed: Sep. 15, 1993

[51] Int. Cl.⁵ ............................................ G01N 15/08
[52] U.S. Cl. ............................................................ 73/38
[58] Field of Search ............................ 73/38, 823, 37.5

[56] References Cited

U.S. PATENT DOCUMENTS

| | | | |
|---|---|---|---|
| 2,880,609 | 4/1959 | Byrkett et al. | 73/38 |
| 2,888,823 | 6/1959 | Hertel | 73/38 |
| 2,919,573 | 1/1960 | Berkley et al. | 73/38 |
| 3,039,293 | 6/1962 | Reddick et al. | 73/38 |
| 3,065,629 | 11/1962 | Neil | 73/38 |

Primary Examiner—Hezron E. Williams
Assistant Examiner—Michael J. Brock
Attorney, Agent, or Firm—Ross, Howison, Clapp & Korn

[57] ABSTRACT

A micronaire testing apparatus includes a vertically movable carriage for receiving a test chamber formed by two telescoping cylinders. A scale is positioned below the carriage so that the chamber may be automatically weighed. Based on the weight information recorded for a sample, cylinders are telescoped together to produce an air flow test chamber of volume calculated to produce a constant density sample. A pivoting lid is used to close the top of the test chamber, and is spring biased to the open position. A latch bar is biased to a position firmly holding the lid in its closed position, and the carriage presses the test chamber against the lid to produce a peripheral seal of the lid.

14 Claims, 7 Drawing Sheets

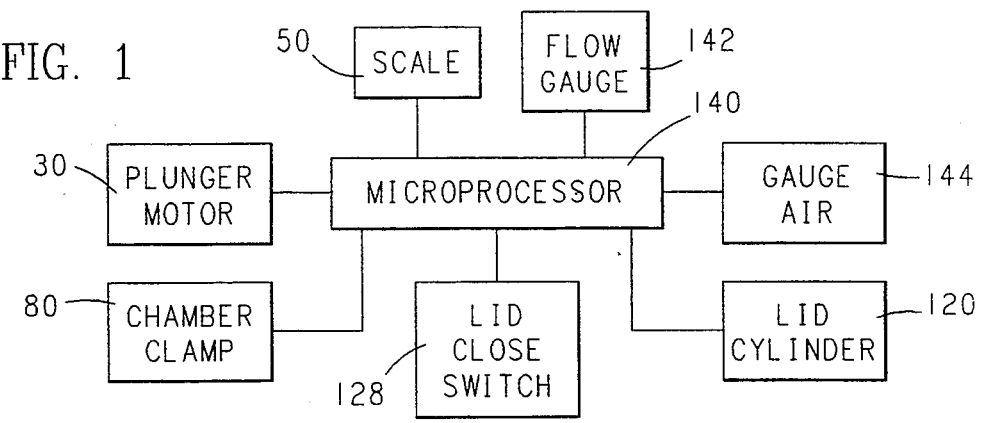
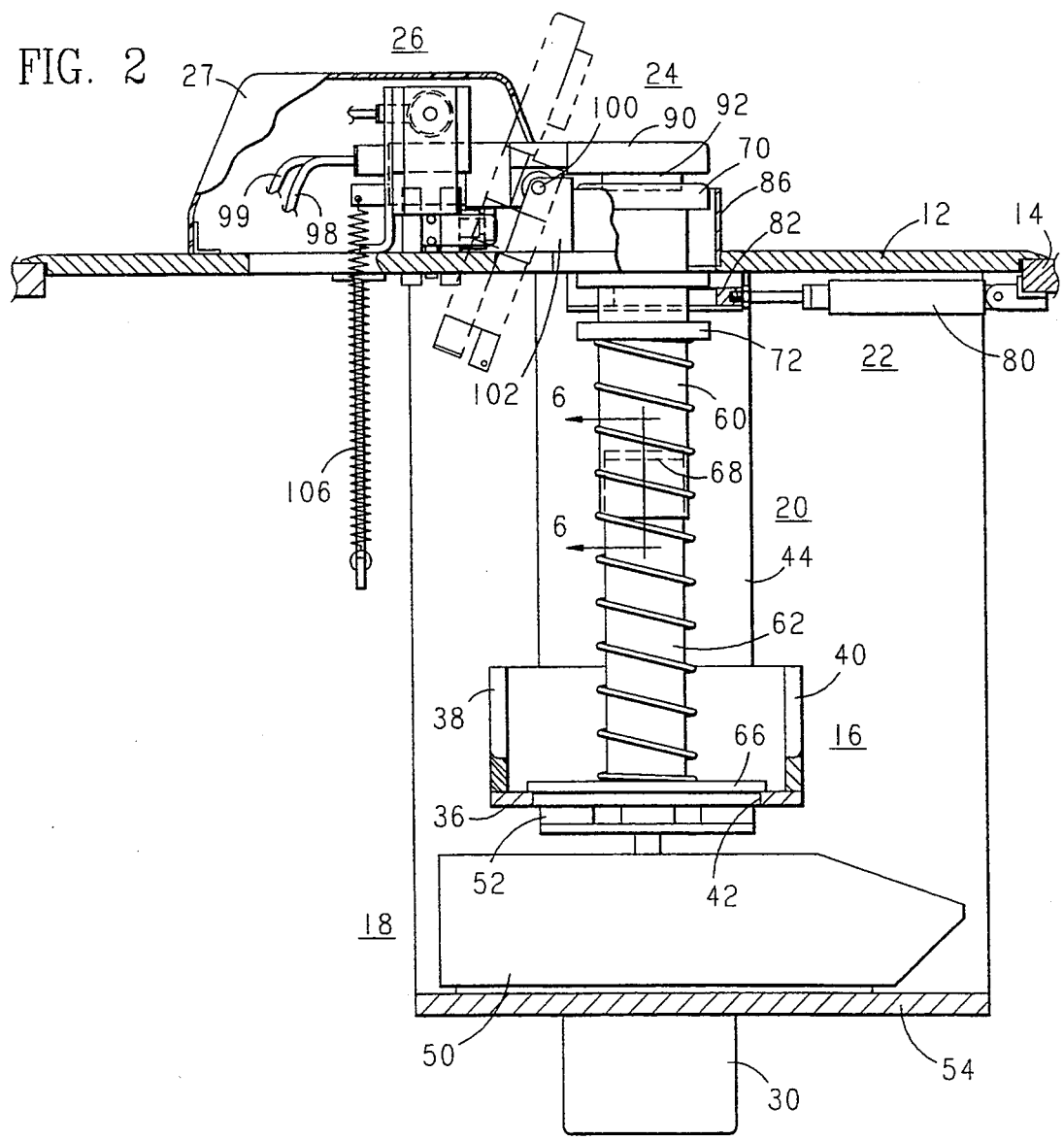

FIBER MICRONAIRE MEASURING APPARATUS AND METHOD

TECHNICAL FIELD OF THE INVENTION

This invention relates to apparatus and methods for testing of the micronaire property of fibers.

BACKGROUND OF THE INVENTION

The testing of cotton fiber physical properties is practiced in the cotton industry for the purpose of evaluation in acceptance testing of cotton. One characteristic which is often tested in cotton fibers is micronaire. In micronaire testing, the air flow resistance of a compressed plug of cotton fibers placed in a closed flow chamber is determined by measuring air flow rate through the plug at a fixed pressure. In effect, the micronaire property is indicative of the fineness of the fiber.

In conventional micronaire measurement systems, a sample of cotton fiber is randomly selected from a cotton lot and weighed. The weighed sample is then transferred to a compression chamber which consists of a cylinder having a plunger for compressing the sample to a fixed volume. The sample is compressed to the predetermined volume. Air is then forced from one end of the chamber to the other through the compressed fiber plug, and the air flow rate is measured to permit calculation of a micronaire value.

In conventional systems, the operator first places a selected sample on the scale for weight determination, and then transfers the sample into a test chamber. Because the conventional test chamber compresses the plug to a constant volume, a determination of the micronaire value requires regression analysis in the calculation software to account for different test plug densities based on the variation in weight of samples selected. Indeed, in order for the testing to occur on a sample of acceptable density, the system must operate upon samples within a relatively restricted weight range because of the fact that each plug is compressed to the same volume.

With the advent of this invention, significant manipulative steps by the operator may be eliminated. Moreover, the test chamber is designed in such a way that each sample is actually tested at a constant density, the test plug when compressed having a variable volume determined by the weight of the sample selected. Both the weighing step and the air flow test are carried out in the same test chamber, and the equipment automatically ejects the fiber from the chamber at the conclusion of the test.

SUMMARY OF THE INVENTION

In accordance with the invention, a fiber micronaire measuring device is provided having a chamber with a movable wall to vary the volume thereof, adapted to receive a fiber sample. A platform scale is positioned below the chamber and a carriage is provided for placing the chamber on the platform of the scale to weigh the chamber. The device includes means for moving the carriage on and off the scale, and driving the movable wall to reduce the volume of the chamber. Air flow means force air through the chamber and means are provided for measuring the air flow rate. In a particular aspect of the invention, control means are provided which cause the drive means to reduce the volume of the chamber to a volume dependent upon the sample weight determined by the scale, so that the sample is tested at a predetermined density.

In a specific configuration of the invention, the test chamber is formed by telescoping cylinders, one of which carries the movable wall for compressing the fiber sample. The movable wall may also be controlled so that it ejects the sample from the test chamber after the testing sequence is completed.

The invention contemplates a mechanism for producing a peripheral seal of a movable lid closing the test chamber. A pivoting lid is movable between an open position and a closed position adjacent a first end of the chamber, and a latch bar is movable to a latched position holding the lid in the closed position. Means are provided for biasing the chamber to press the first end of the chamber against the lid when it is in its closed position to produce a peripheral seal of lid and chamber. In a specific aspect of the invention, the lid is biased to its open position. Means are provided for moving the latch bar away from the latched position upon completion of the testing sequence, and further means are provided for sensing movement of the latch bar to its latched position to initiate a testing sequence.

In a specific embodiment of the invention, latch biasing means are provided to bias the latch bar to its latched position and the lid includes a surface which, in the open position of the lid, abuts the latch bar to prevent movement of the latch bar to the latched position until the operator manually moves the lid towards its closed position.

In accordance with the invention, a method for measuring the micronaire of a fiber sample comprises placing the sample into a chamber having a movable wall, and lowering the chamber so that it rests on a scale to determine and record the weight of the sample. The single chamber is then sealed, the sample compressed, air is forced through the chamber and the flow rate is measured.

BRIEF DESCRIPTION OF THE DRAWINGS

For a more complete understanding of the present invention and for further advantages thereof, reference is now made to the following Description of the Preferred Embodiments taken in conjunction with the accompanying Drawings in which:

FIG. 1 is a schematic illustration showing interconnection of the control elements of an apparatus constructed in accordance with the invention;

FIG. 2 is a side view of an apparatus embodying the invention with the protective cover partially broken away and the lid in its closed test position;

Figure 11:
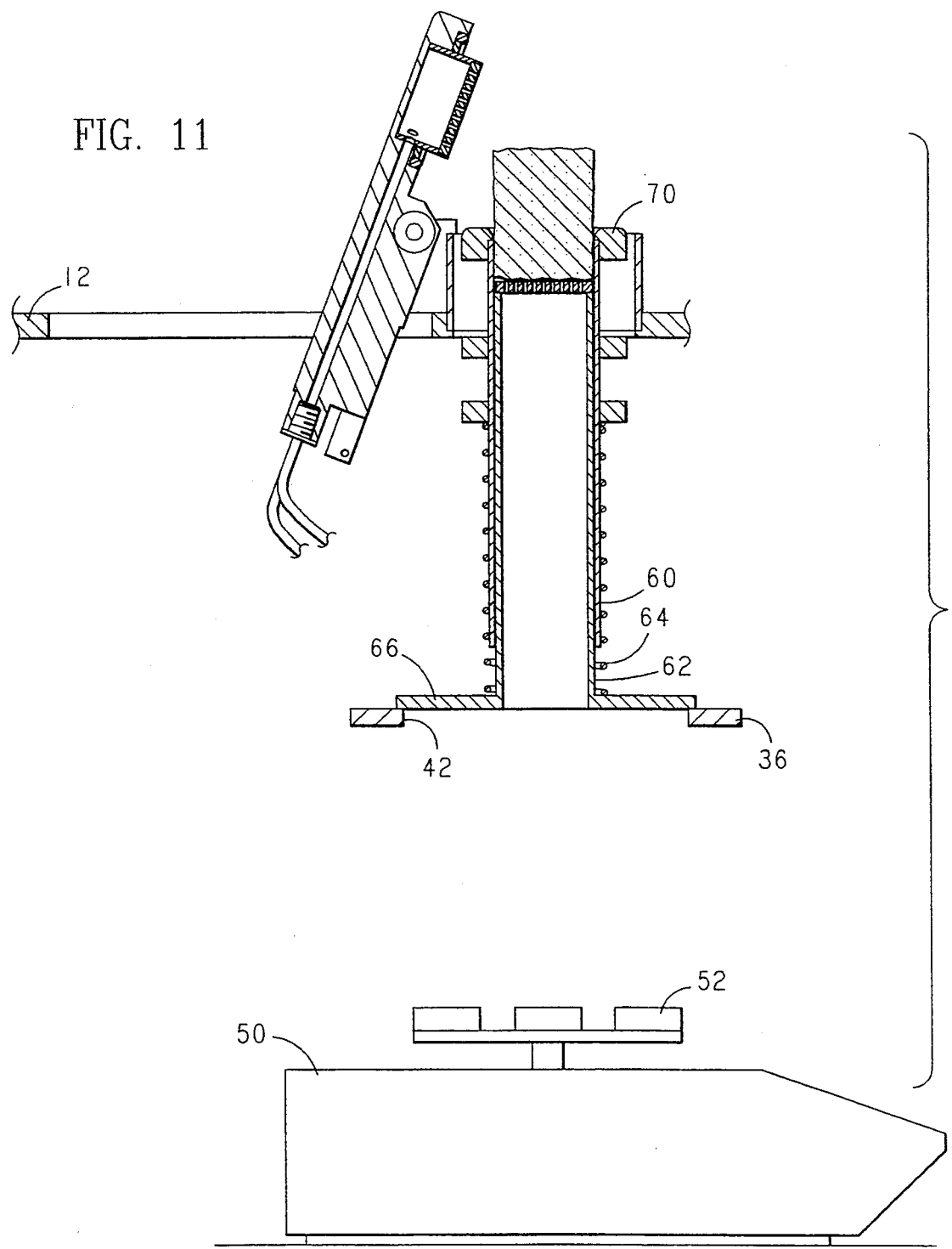

10 illustrating the testing position and FIG. 11 illustrating the eject position.

DESCRIPTION OF THE PREFERRED EMBODIMENTS

Figures 3, 4:
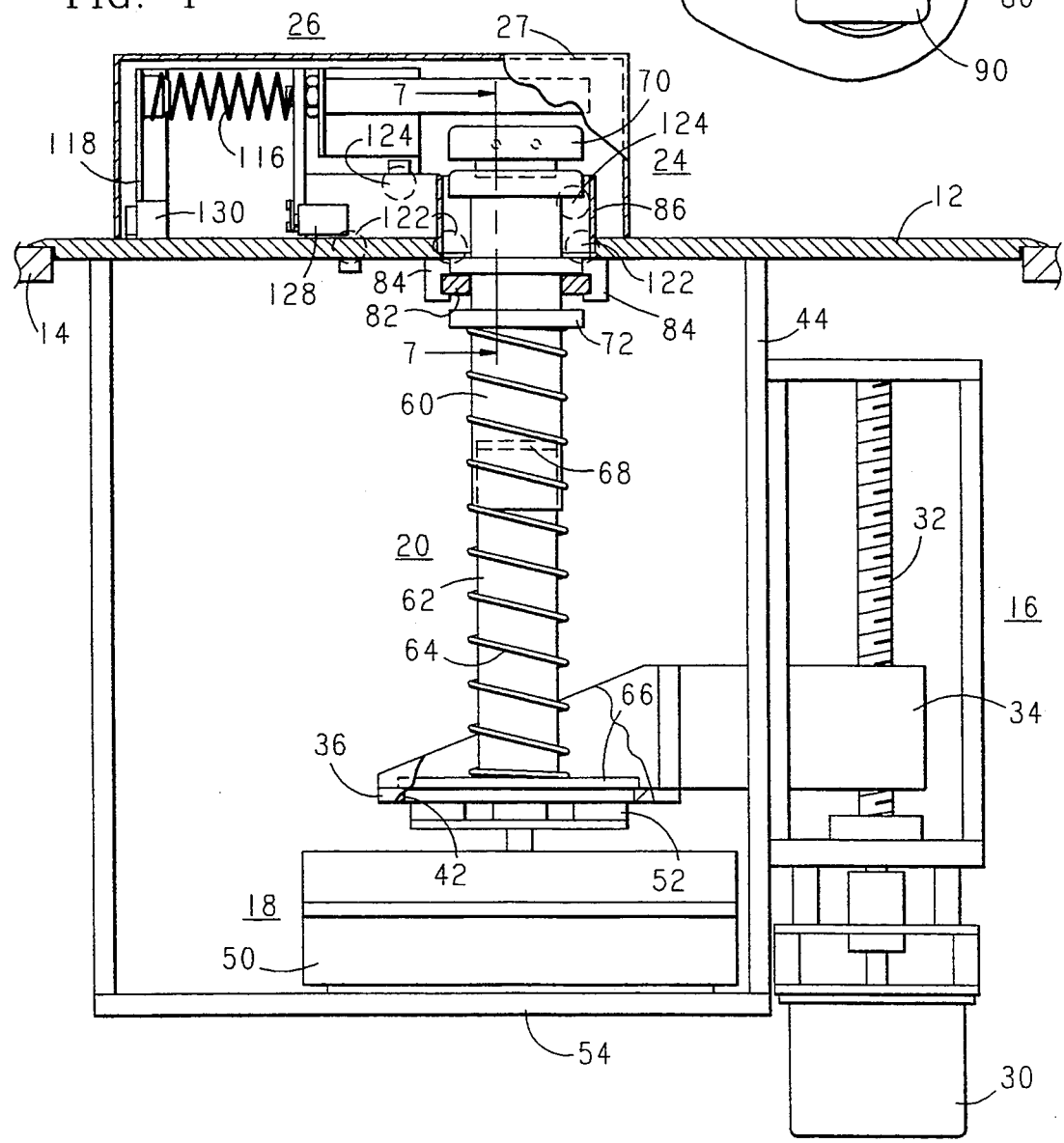
FIG. 3 is a top view of the apparatus shown in FIG. 2.
FIG. 4 is a front view of the apparatus shown in FIG. 2.
Figure 5:
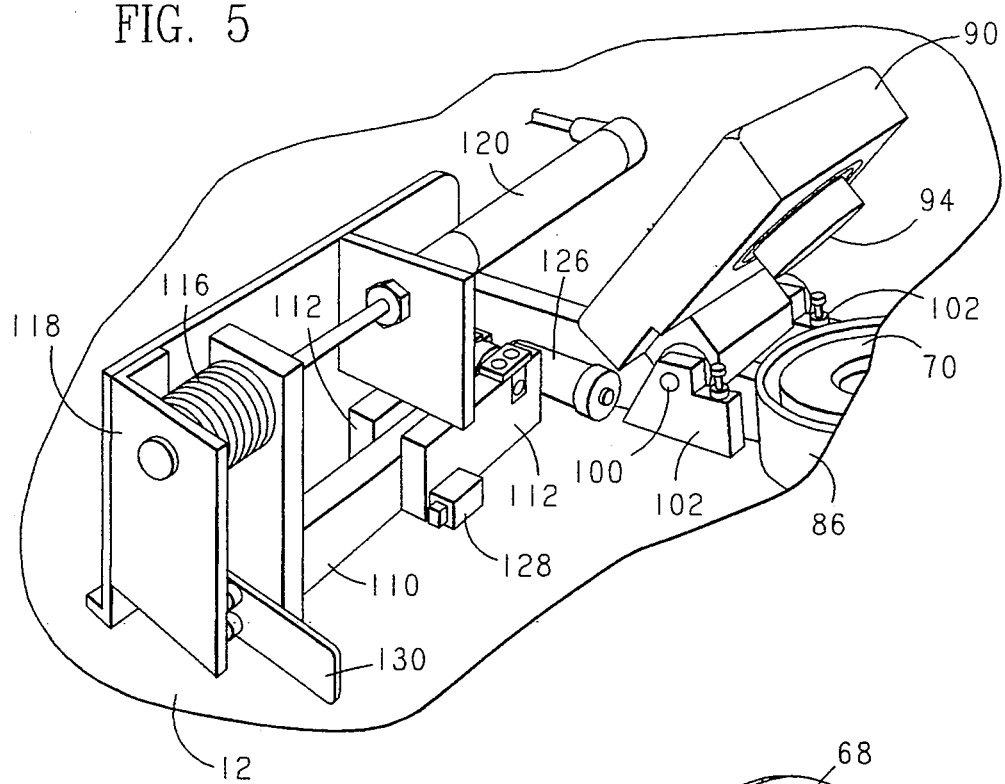
FIG. 5 is a perspective view of the upper portion of the apparatus with protective cover removed and the lid in its open, home position.
Figure 6:
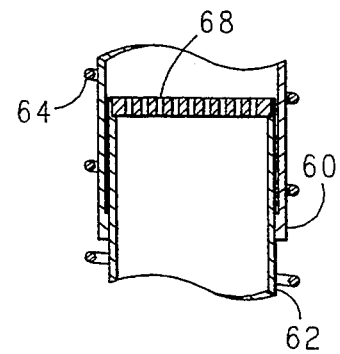
FIG. 6 is a cross-section taken along line 6—6 in FIG. 2.
Figure 7:
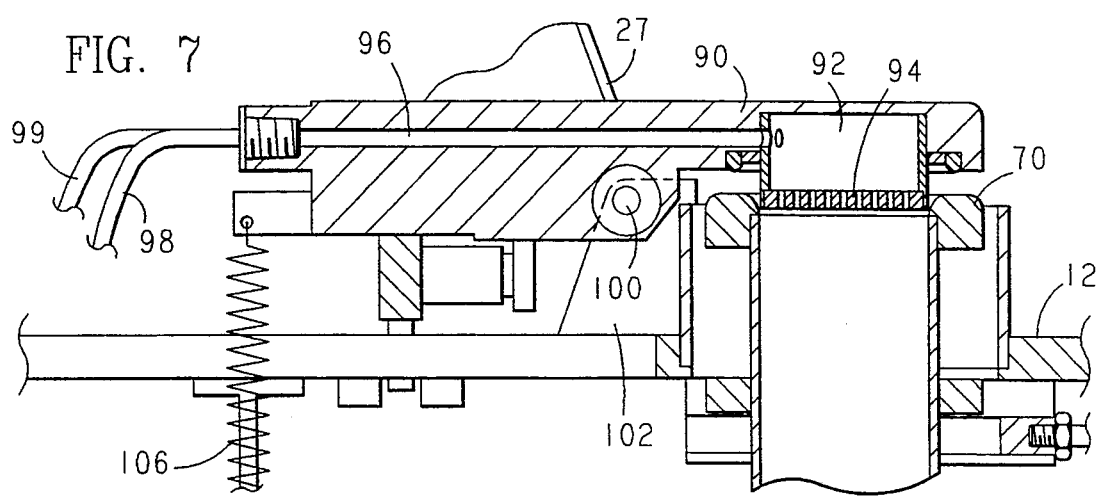
FIG. 7 is a cross-section taken along the line 7—7 in FIG. 4.

As shown in FIGS. 2 through 4, a micronaire testing apparatus is arranged with components positioned above and below a work surface 12. Work surface 12 may be the top of a freestanding instrument for measuring micronaire, or be a module installed in a console top 14 as a part of a fiber testing system having work stations for carrying out other property testing on fiber samples. The portions of the equipment installed below work surface 12 are preferably positioned in a cabinet (not shown) having doors for access to the lower components. The major components of the apparatus below top 12 are the carriage assembly 16, the platform scale assembly 18, the test chamber assembly 20 and the chamber clamp assembly 22. A lid assembly 24 is mounted to the top of work surface 12 as is a lid latch assembly 26. Removable protective cover 27 shields major portions of assemblies 24 and 26.

Carriage assembly 16 includes a bidirectional stepper motor 30 which drives vertical lead screw 32. Carriage 34 is threaded on lead screw 32, so that as motor 30 turns lead screw 32, carriage 34 is raised or lowered. Carriage 34 is guided vertically by rails 44. Test chamber receiving deck 36 extends laterally from carriage 34 between vertical walls 38 and 40. Deck 36 include a large central aperture 42.

Scale assembly 18 comprises a conventional digital scale 50 having an upper scale platform 52 for receiving articles to be weighed. The relative dimensions of scale platform 52 and carriage deck aperture 42 are significant. Aperture 42 must be larger than platform 52 so that carriage 34 may be lowered to place deck 36 below the level of scale platform 52, transferring an object otherwise borne by deck 36 directly onto platform scale 52. Scale 50 is positioned on a scale mounting surface 54 in alignment with deck aperture 42.

Chamber assembly 20 is formed by upper cylinder 60 and lower cylinder 62 biased apart by cylinder spring 64 which surrounds them. The lower end of lower cylinder 62 is formed with a base flange 66 having a diameter larger than deck aperture 42. Base flange 66 is positioned on deck 36 so that it is raised and lowered as motor 30 raises and lowers carriage 34. Upon lowering of deck 36 below the level of scale platform 52, base flange 66 (and thus the weight carried thereby) will be transferred to the scale platform 52. The upper end of lower cylinder 62 is closed by a foraminous plate 68. The end of lower cylinder 62 adjacent base flange 66 is open, so that air is free to travel from foraminous plate 68 to exit lower cylinder 62 adjacent base flange 66.

Upper cylinder 60 is of a slightly larger diameter than lower cylinder 62, so that the cylinders 60 and 62 slidingly telescope together. The vertical wall of upper cylinder 60 forms the side walls of the test chamber in which fibers to be tested are placed. Foraminous plate 68 forms a movable bottom wall of the test chamber, so that the volume encompassed by upper cylinder 60 above plate 68 may be varied by relative movement of the cylinders. The upper end of cylinder 60 is provided with a polished circumferential sealing lip 70 for providing a peripheral seal to the top of the test chamber. Clamping flange 72 is also provided on upper cylinder 60. Flange 74 is spaced above flange 72. Upper cylinder 60 is biased upwardly away from base flange 66 by spring 64 acting on flange 72. It will be appreciated that the arrangement of test chamber assembly 20 permits lower cylinder 62 to act as a compressing plunger to reduce the volume of the test chamber defined by upper cylinder 60 and plate 68 when carriage 34 is raised to elevate lower cylinder 62. Chamber clamp assembly 22 is mounted directly underneath work surface 12 and includes a double acting pneumatic cylinder 80 which drives a clamping fork 82 between a clamped and unclamped position. Clamp fork 82 is guided by guide rails 84. In the normal clamped position of clamp assembly 22, clamp fork 82 surrounds upper cylinder 60 between flanges 72 and 74. Flange 72 serves with fork 82 to prevent ejection of upper cylinder 60 from the apparatus. Flange 74 acts with fork 82 to hold cylinder 60 up for loading of the test chamber, avoiding "bouncing" of cylinder 60 on spring 64.

Top 12 is provided with an aperture through which the upper cylinder 60 extends, so that the operator has access to the top of the test chamber. Upstanding cylindrical wall 86 surrounds the opening in work surface 12 to reduce the incidence of debris falling through the surface 12 into the apparatus below.

Lid assembly 24 includes a pivoting lid 90. An air inlet 92 extends from the lower surface of one end of lid 90, and is dimensioned so that it fits snugly within the upper end of upper cylinder 60 when the lid 90 is in its closed position illustrated in solid lines in FIG. 2. Inlet 92 bears on its face a foraminous plate 94 for passing air into upper cylinder 60. An O-ring 95 is positioned around inlet 92 to provide a peripheral seal of the lid 92 and sealing lip 70 of upper cylinder 60. An internal air passage 96 extends the length of lid 90 between air supply line 98 and air inlet 92. A pressure sensing line 99 extends into lid 90, with access to inlet 92 at aperture 101, in order to regulate the pressure of air being supplied at inlet 92. Lid 90 is pivoted on pivot pin 100 journalled in pivot support brackets 102 upstanding from surface 12. The end of lid 90 opposite air inlet 82 is provided with spring mounting tab 104 which holds one end of lid biasing spring 106. The opposite end of spring 106 is secured to stationary structure underneath surface 12 so that the lid is spring biased to the open position illustrated in phantom in FIG. 2.

Lid latch assembly 26 includes a horizontally moving latch bar 110 positioned atop surface 12 between vertical guide plates 112. Latch bar 110 is carried by latch bar mounting plate 114. Latch bar mounting plate 114 is movable between an open and closed position, and is biased toward the closed position by latch biasing spring 116 positioned between mounting plate 114 and stationary vertical spring mounting flange 118. A single acting pneumatic cylinder 120 is mounted directly above the latch bar travel path so that activation of the cylinder pushes the latch bar mounting plate 114 away from the lid, compressing spring 116 and moving latch bar 110 away from lid 90 to its open position.

In the closed position of latch bar 110, the upper surface of latch bar 110 is snugly received under the lid 90 to retain lid 90 firmly in the closed position. Roller bearings 122 are mounted in surface 12 for smoothly gliding the latch bar 110 in its travel path. Similar roller bearings 124 are mounted on the underside of lid 90 and adjacent cylinder 120 engaging the upper surface of latch bar 110. The latch bar is thus constrained for smooth movement on a horizontal travel path atop surface 12. The end of latch bar 110 remote from latch bar mounting plate 114 also carries roller bearing structure 126. Roller bearing structure 126 extends laterally of the latch bar 110 so that when the latch bar 110 is retracted to its unlatched position, and lid 90 is pivoted to its open position under the influence of biasing spring 106, the side of lid 90 adjacent the latch bar travel path engages roller bearing structure 126 to prevent movement of latch bar 110 to the latched position. This eliminates the necessity of continuous powering of cylinder 120. A proximity switch 128 is carried by one of the latch bar guide plates 112. Horizontally extending switch tab 130 carried by latch bar mounting plate 114 extends laterally from the travel path of latch bar 110 so that, in the latched position of latch bar 110, it engages proximity switch 128 to provide positive indication of the latching of lid 90 in its closed position.

As illustrated in FIG. 1, the active elements of the testing apparatus are under the control of microprocessor 140. Microprocessor 140 receives the information from switch 128 that the lid is closed and latched. Microprocessor 140 controls the operation of chamber clamp cylinder 80 between its clamped and unclamped positions. The motor 30 is stepped in accordance with instructions received from microprocessor 140. Readings from the scale 50 are received and recorded by the microprocessor 140 as well as the air flow readings from a conventional flow gauge 142 mounted in the air supply line 98. Microprocessor 140 also controls the turning on of gauge air switch 144. Microprocessor 140 activates cylinder 120 which acts to unlatch latch bar 110 and thus opens lid 90 on completion of testing.

Figure 8:
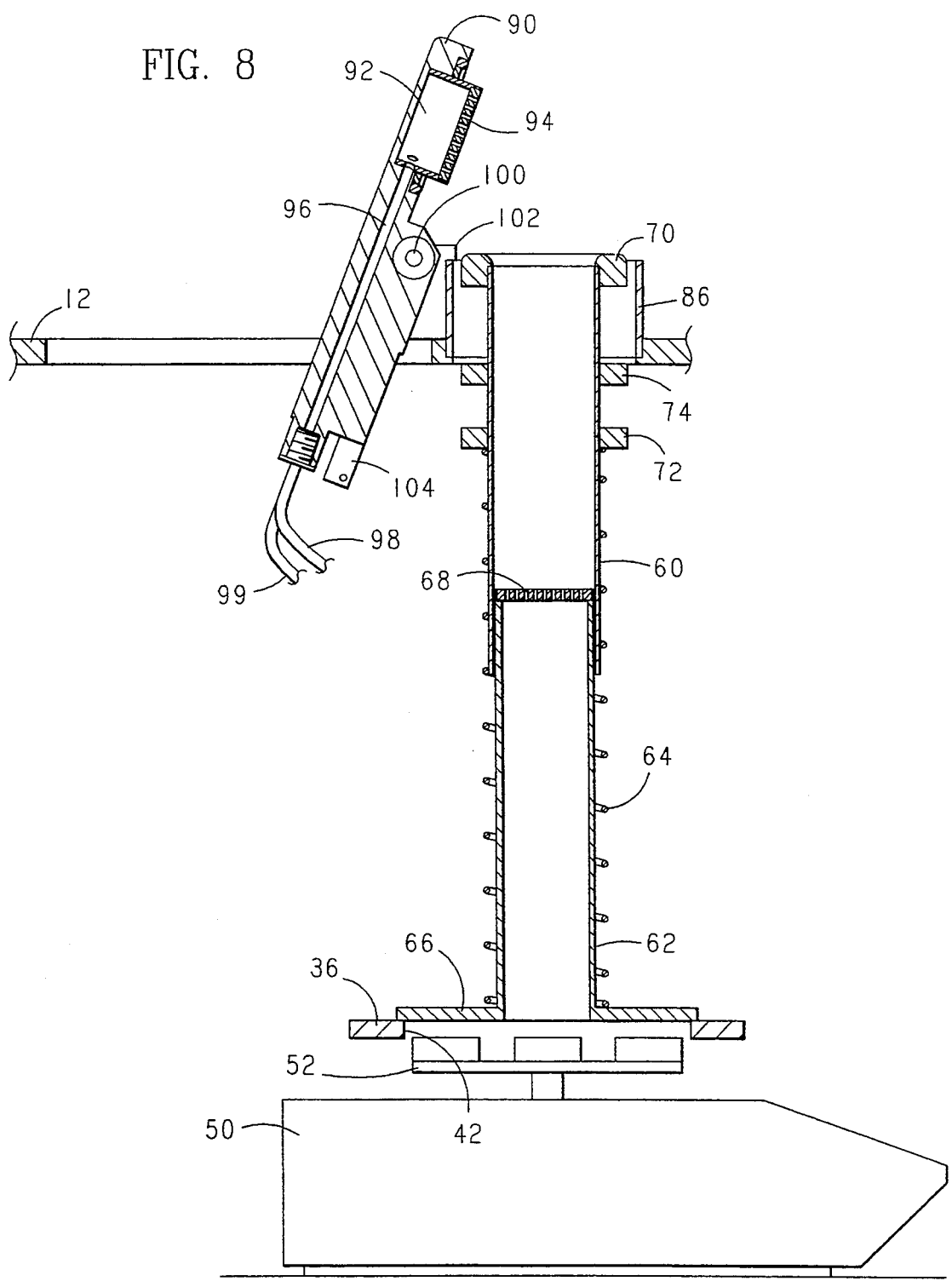
FIGS. 8 through 11 schematically illustrate the position of the apparatus in each of its four principal stages of operation, FIG. 8 illustrating the open position with lid open, FIG. 9 illustrating the weighing position, FIG.

On initial powerup of the apparatus, the microprocessor 140 controls the elements of the system so that they are placed in their rest or home position illustrated in FIG. 8. Lid 90 is open and latch cylinder 120 is maintained unlatched, the carriage chamber is clamped by chamber clamp 80 and the stepping motor 30 positions carriage 34 as illustrated in FIG. 8. Gauge air 144 is turned off so that air does not travel through lid 90 in its rest position.

Figure 9:
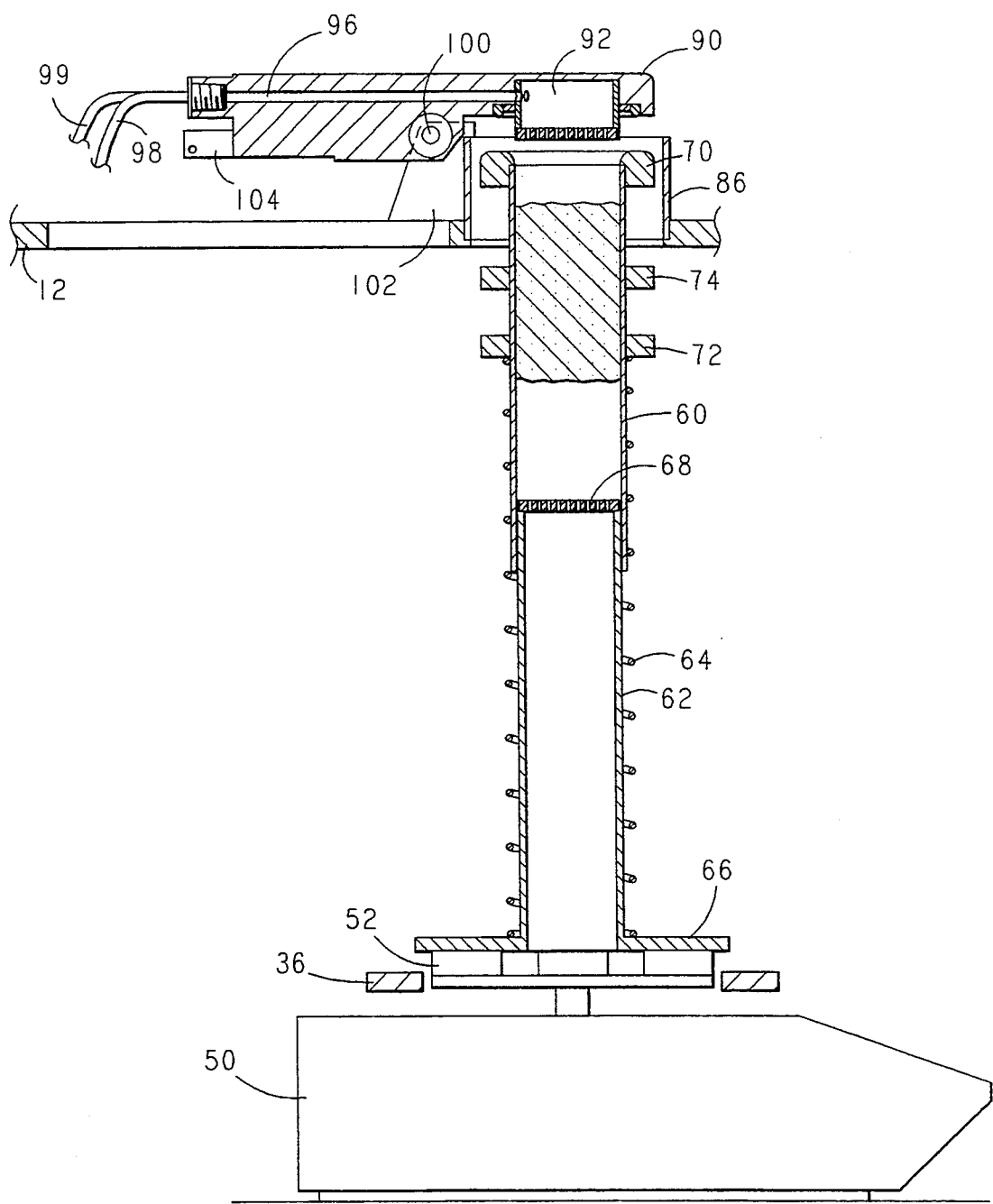

In order to provide weight readings for samples placed in the test chamber, the apparatus also automatically carries out a taring sequence for determining the weight of the apparatus which rests on scale 50 during the weighing step of the test. Weighing is carried out by lowering the test chamber receiving deck 36 below the platform 52 of scale 50 as shown in FIG. 9. In this position, base flange 66 rests on platform 52, and the scale 50 records the tare weight of lower cylinder 62, upper cylinder 60 and cylinder spring 4. Of course, chamber clamp cylinder 80 is in the unclamped position during weighing. The tare weight is stored in scale 50, and the chamber is returned to the home position illustrated in FIG. 8.

The apparatus is now ready to begin testing, having stored its tare weight in scale 50. The testing sequence is initiated by an operator by selecting a sample, placing it into the test chamber and manually lowering lid 90 to its closed position. The closing of the lid permits latch bar 110 to move to its closed position under the influence of latch bar biasing spring 116. The completion of the latch bar 110 travel to the latched position to hold the lid in its closed position is signalled to microprocessor 140 when the latch switch tab 130 engages proximity switch 128. The microprocessor then directs the apparatus to commence the test sequence. Clamp cylinder 80 unclamps, and motor 30 is driven to lower deck 36 below the level of scale platform 52 as shown in FIG. 9. This transfers the weight of the sample plus tare weight to the scale 50. The scale 50 senses the weight, subtracts the stored tare weight, and sends a sample weight signal to microprocessor 140 to record sample weight for the run.

Although the operating characteristics of this system have a much wider variation in permitted sample weight than in prior art systems, it still must operate within certain weight limits. If the reported sample weight is outside such limits, the testing on this sample is aborted, and the system moves directly to the sample eject position of FIG. 11 which will be described below. The operator is signalled that the sample weight is below or above limits and the apparatus returns to the home position.

Figure 10:
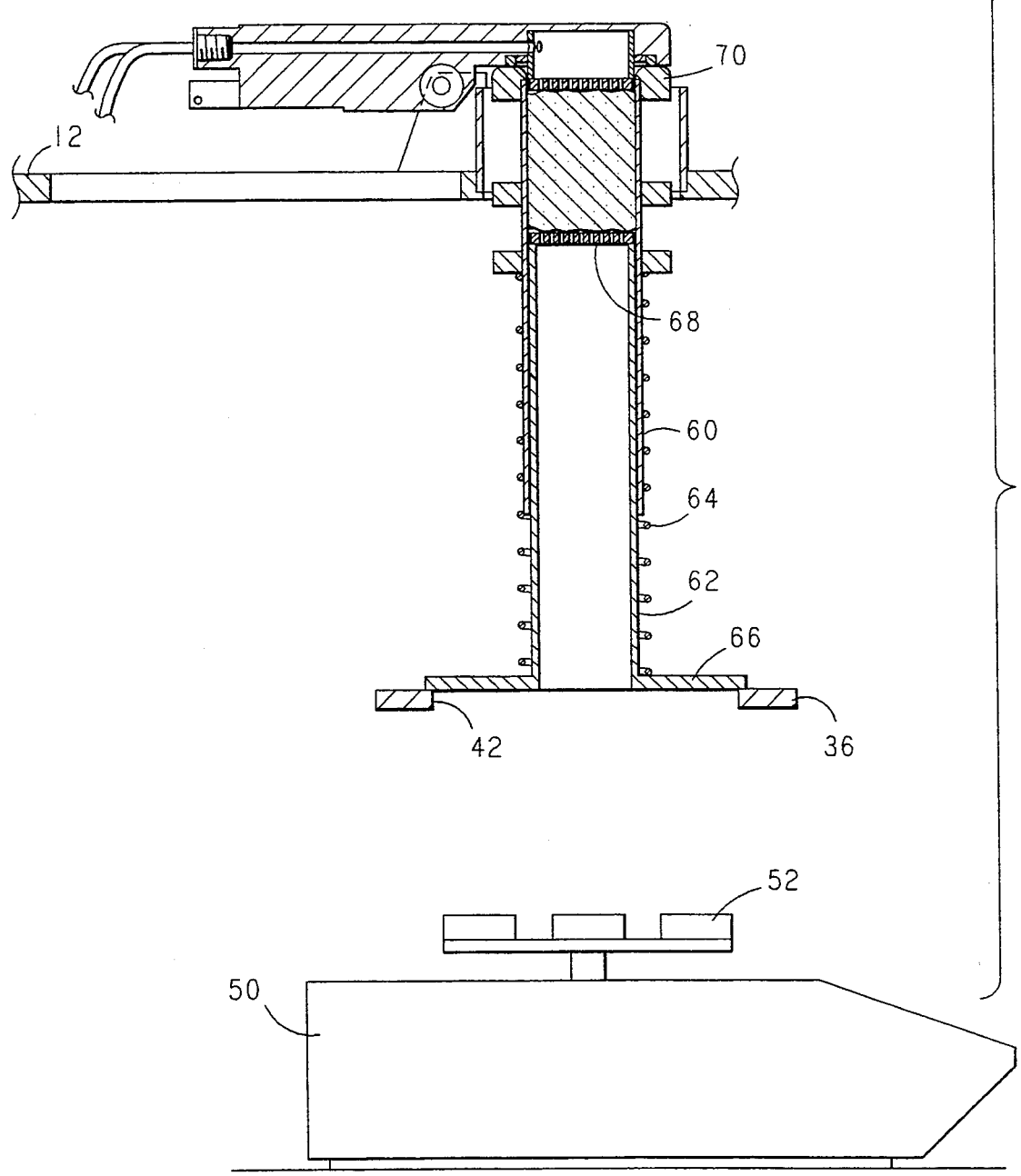

If the sample is within the broad weight limits, the motor 30 is operated to raise carriage 34 and lift the test chamber off of scale platform 52. The upward movement of carriage 34 is continued to cause the foraminous plate 68 of lower cylinder 62 to compress the sample against lid 90. The extent of upper advancement of lower cylinder 62 to compress the sample is controlled by microprocessor 140 to produce a sample plug of predetermined density. Thus, the effective test volume of the chamber is variable under the control of the microprocessor 140, based upon the weight information recorded from scale 50. When the movement of carriage 34 has produced a test chamber of volume dictated by the sample weight, such as shown in FIG. 10, the processor 140 turns gauge air 144 on so that constant pressure air is directed to air supply line 98 and through air passage 96 in lid 90. The air passes through air inlet 92, foraminous plate 94 and the test sample in the test chamber, and exits through foraminous plate 68 of lower cylinder 62. The gauge 142 sends an air flow rate signal to processor 140 for calculation of the micronaire value. The micronaire value is recorded by microprocessor 140, gauge air is turned off and the carriage 34 is lowered by motor 30 a short distance to relieve pressure on lid 90. Microprocessor 140 activates latch cylinder 120 to unlatch latch bar 110 against the biasing pressure of latch spring 116. As latch bar 110 moves away from lid 90, lid spring 106 causes the lid to open. Carriage 34 then raises to the sample eject position illustrated in FIG. 11, removing the cotton sample from the test chamber. The test is completed with the micronaire property recorded, and the apparatus is returned to its home or rest position.

One alternate procedure for the sample weighing portion of the test sequence which may be utilized is to activate cylinder 120 to open lid 90 before sample weighing commences. This reduces the possibility that a part of the sample may cling to the lid 90 and distort the weight reading. If this procedure is employed, the instrument cues the operator to close the lid again after the weighting is complete, whereupon the instrument will move to the air test stage of operation (FIG. 10).

It will be appreciated that the apparatus of this invention permits an extremely efficient technique for determination of micronaire. Manipulations by the operator are limited to placing a fiber sample in the test chamber and manually closing the lid. In all other respects, the apparatus operates entirely automatically. There is no necessity for carrying out separate weighing and testing steps. Moreover, the actual air flow testing is carried out at constant sample density, simplifying the computational software for determining micronaire from a given air flow reading. The variable volume characteristic of the test chamber permits acceptable readings to be carried out on a significantly broader range of sample weights and thus reduces the instances in which selection of a second sample is necessitated by an out-of-weight condition of a first sample. The equipment ejects the sample and places itself in a ready condition for subsequent testing. It will be appreciated that the time and motion efficiency of this testing apparatus and method is vastly superior to conventional techniques and apparatus.

Whereas the present invention has been described with respect to specific embodiments thereof, it will be understood that various changes and modifications will be suggested to one skilled in the art and it is intended to encompass such changes and modifications as fall within the scope of the appended claims.

We claim:

1. A fiber micronaire measuring device, comprising:
   (a) a chamber adapted to receive a fiber sample, the chamber having a movable wall to vary the volume thereof;
   (b) a platform scale adjacent the chamber;
   (c) a carriage for placing the chamber on the platform of the scale to weigh the chamber;
   (d) means for moving the carriage on and off the scale and for driving the movable wall to reduce the volume of the chamber;
   (e) air flow means for forcing air through the chamber; and
   (f) means for measuring the air flow rate.

2. The device of claim 1, further comprising control means for the driving means which causes the driving means to reduce the volume of the chamber to a volume dependent on sample weight determined by the scale, whereby the sample may be tested at a predetermined density.

3. The device of claim 1, in which the chamber is formed by telescoping cylinders, one of which carries said movable wall.

4. The device of claim 3, further comprising control means for causing the cylinder carrying the moving wall to eject a sample after the air flow rate is measured.

5. A fiber micronaire measuring device, comprising:
   (a) a chamber adapted to receive a fiber sample, the chamber having a movable wall to vary the volume thereof;
   (b) a platform scale positioned below the chamber;
   (c) a carriage for lowering the chamber to the platform of the scale to weigh the chamber;
   (d) means for driving the movable wall to reduce the volume of the chamber;
   (e) control means for the driving means which causes the driving means to reduce the volume of the chamber to a volume dependent on the weight of a fiber sample placed in the chamber, whereby the sample may be tested at a predetermined density; and
   (f) air flow means for forcing air through the chamber.

6. The apparatus of claim 5, wherein said control means can cause the driving means to eject a sample from the chamber.

7. A fiber micronaire measuring device, comprising:
   (a) a first cylinder defining the side walls of a chamber;
   (b) a second cylinder axially movable in the first cylinder, and having a foraminous plate at its upper end inside the first cylinder to form an open floor for the chamber;
   (c) a movable lid adjacent the top of the first cylinder, adapted to forming a tight peripheral seal with the end of the first cylinder, and having an inlet for introducing forced air into the chamber at the top thereof;
   (d) a carriage supporting the second cylinder;
   (e) a platform scale positioned below the carriage;
   (f) drive means for lowering the carriage to position the second cylinder on the platform of the scale to determine the weight of a fiber sample placed in the chamber, and for subsequently raising the carriage and second cylinder to raise the floor of the chamber to reduce the chamber volume in dependence on the determined sample weight to compress the sample to a predetermined density;
   (g) air flow means for forcing air through the lid inlet; and
   (h) means for measuring the air flow rate.

8. A micronaire test apparatus, comprising:
   a test chamber for receiving a fiber sample; means for compressing the sample in the chamber; a pivoting lid movable between an open position and
   a closed position adjacent a first end of the test chamber;
   a latch bar movable to a latched position holding the lid in said closed position;
   means biasing the chamber to press the first end of the test chamber against the lid when the lid is in its closed position to produce a peripheral seal of lid and chamber.

9. The apparatus of claim 8, further comprising lid biasing means acting on the lid to bias it to its open position.

10. The apparatus of claim 8, further comprising means for moving the latch bar away from the latched position upon completion of a testing sequence, and means for sensing movement of the latch bar to the latched position to initiate a testing sequence.

11. The apparatus of claim 8, further comprising latch biasing means biasing the latch bar to its latched position, and wherein the lid includes a surface which, in the open position of the lid, abuts the latch bar to prevent movement of the latch bar to the latched position until the lid is moved toward the closed position.

12. The apparatus of claim 8, wherein the test chamber is comprised of two telescoping cylindrical walls and one of said walls is spring-biased toward the lid, and the other carries a movable floor for the chamber.

13. A method of measuring the micronaire of a fiber sample, comprising:
   (a) placing the sample into a chamber having a movable wall;
   (b) placing the chamber on a scale;
   (c) determining and recording the weight of the sample;
   (d) moving the chamber to a position adjacent a movable lid;
   (e) sealing the lid tightly on the chamber;
   (f) compressing the sample by pushing the movable wall toward the sample a distance determined by the recorded weight;
   (g) forcing air into the chamber at a predetermined pressure through the lid; and
   (h) measuring the air flow rate.

14. A method of measuring the micronaire of a fiber sample comprising:
   (a) placing the sample in a single chamber;

(b) weighing the chamber to determine the weight of the sample;

(c) recording the sample weight;

(d) sealing a first end of the single chamber;

(e) compressing the sample against the first end of the chamber;

(f) forcing air through the chamber at a predetermined pressure; and (g) measuring the air flow rate.

* * * * *